（12）United States Patent
Maeda et al.

(10) Patent No.: US 7,491,832 B2
(45) Date of Patent: Feb. 17, 2009

(54) SULFONATE COMPOUND AND FLUORESCENT PROBE USING THE SAME

(75) Inventors: Hatsuo Maeda, Suita (JP); Kazumasa Hirata, Suita (JP); Kazuhisa Miyamoto, Suita (JP)

(73) Assignee: Osaka Industrial Promotion Organization, Osaka (JP)

( * ) Notice: Subject to any disclaimer, the term of this patent is extended or adjusted under 35 U.S.C. 154(b) by 13 days.

(21) Appl. No.: 11/328,995

(22) Filed: Jan. 10, 2006

(65) Prior Publication Data

US 2006/0105410 A1 May 18, 2006

Related U.S. Application Data

(63) Continuation of application No. PCT/JP2004/009661, filed on Jul. 7, 2004.

(30) Foreign Application Priority Data

Jul. 11, 2003 (JP) .............................. 2003-273659

(51) Int. Cl.
*C07D 265/34* (2006.01)
*C07D 311/88* (2006.01)

(52) U.S. Cl. ....................... 549/223; 549/344; 549/388; 549/392; 549/393

(58) Field of Classification Search ................. 549/223, 549/344, 388, 392, 393
See application file for complete search history.

(56) References Cited

U.S. PATENT DOCUMENTS

| 4,618,622 A | 10/1986 | Schlecker et al. |
| 5,453,461 A | 9/1995 | Heiliger et al. |
| 5,576,424 A | 11/1996 | Mao et al. |
| 5,684,040 A | 11/1997 | Grabowski et al. |
| 5,986,094 A | 11/1999 | Ghoshal et al. |
| 6,130,101 A | 10/2000 | Mao et al. |

FOREIGN PATENT DOCUMENTS

| JP | 6-281581 | 10/1994 |
| JP | 2000-316598 | 11/2000 |
| WO | 98/39317 | 9/1998 |
| WO | 98/39319 | 9/1998 |

OTHER PUBLICATIONS

Maeda et al. Angew. Chem. Int. Ed. 2004, 43, 2389-2391.*
Nakano, M., "Detection of Active Oxygen Specics in Biological Systems", Cellular and Molecular Neurobiology, vol. 18, No. 6, 1998, 565-579.
Murrant, et al., "Detection of Reactive Oxygen and Reactive Nitrogen Species in Skeletal Muscle", Microscopy Research and Technique, 55:236-248 (2001).
Tarpey, et al., "Methods of Detection of Vascular Reactive Species", Circ Res. 2001;89:224-236.
Münzel, et al., "Detection of Superoxide in Vascular Tissue", Arterioscler Throb Vasc Biol. 2002;22:1761-1768.
Esposti, M.D., "Measuring mitochondrial reactive oxygen species", Methods 26 (2002) 335-340.
Rothe, et al., "Flow Cytometric Analysis of Respiratory Burst Activity in phagocytes with Hydroethidine and 2', 7'Dichlorofluorescin", Journal of Leukocyte Biology 47:440-448 (1990).
Carter, et al., "Intracellular hydrogen peroxide and superoxide anion detection in endothelial cells", Journal of Leukocyte Biology 55:253-258 (1994).
Bindokas, et al., "Superoxide Production in Rat Hippocampal Neurons: Selective Imaging with Hydroethidine", The Journal of Neuroscience, Feb. 15, 1996, 16(4): 1324-1336.
Al-Mehdi, et al., "Intracellular generation of reactive oxygen species during nonhypoxic lung ischemia", The American Physiological Society, 1997, 272, L294-L300.
Benov, et al., "Critical Evaluation of the Use of Hydroethidine as a Measure of Superoxide Anion Radical", Fee Radical Biology & Medicine, vol. 25, No. 7, pp. 829-831, 1998.
Fukuyama, et al., "2,4-Dinitrobenzenesulfonamides: A Simple and Practical Method for the Preparation of a Variety of Secondary Amines and Diamines", Tetrahedron Letters, vol. 38, No. 33, pp. 5831-5834, 1997.

(Continued)

*Primary Examiner*—Kahsay T Habte
(74) *Attorney, Agent, or Firm*—Hamre, Schumann, Mueller & Larson, P.C.

(57) ABSTRACT

The present invention provides a sulfonate compound including a structure represented by a general formula (I) below.

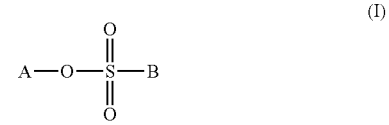

(I)

In the formula (I), an atomic group A-O is an atomic group that forms a fluorescent compound upon cleavage of a covalent bond with a sulfonyl group. There may be one or plural atomic groups B—SO$_3$— bound to an atomic group A. B is a ring substituted by one or plural electron-withdrawing groups. The electron-withdrawing group includes at least one selected from the group consisting of halogens, a carboxyl group, a carbamoyl group, a straight or branched alkylcarbamoyl group, a straight or branched alkanoyl group, a straight or branched alkoxycarbonyl group, a straight or branched alkyl halide group, and —NR$_3^+$ group (the three Rs each denote a hydrogen atom or a straight or branched alkyl group and may be the same or different). When there are plural Bs, the Bs may be the same or different.

3 Claims, 1 Drawing Sheet

OTHER PUBLICATIONS

Maeda, et al., "Hydrogen Peroxide-Induced Deacetylation of Acetyl Resorufin as a Novel Indicator Reaction for Fluorometric Detection of Glucose Using Only Glucose Oxidase", Chem. Pharm. Bull. 49(3) 294-298 (2001).

Maeda, et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", Chem. Pharm. Bull. 50(2) 169-174 (2002).

Maeda, et al., "Development of Fluorescent Probe Specific to Hydrogen Peroxide or Superoxide", on line Jul. 8, 2003, bmas lecture summery, Retrieval day Aug. 6, 2004, www10.showa-u.ac.jp/-bmas/proceedings/III-9.pdf (w/full translation).

Delzenne, et al., Photosensitive polymers I.-Synthesis and Properties of Coumarin-modified Polymers, Industrie Chimique Belge, 1967, 21, 373-378.

Esayan, et al., "Esters of sulfonic acids, SI. Synthesis and Acricidal Propertis of Some P-chlorobenzenesulfonic Acid Esters" Izvestiya akademii Nauk Armyanskoi SSR, Khimicheskie Nauki, 1962, vol. 15, 285-289.

Rendenbach-Müller, et al., "Synthesis of Coumarins as Subtype-Selective Inhibitors of Monoamine Oxidase", Bioorganic & Medicinal Chemistry Letter, vol. 4, No. 10, 1195-1198, 1994.

Matsu-ura, et al., "Blood glucose determination with an acetyl resorufin-glucose oxidase system as a fluorometirc indicator reaction", Bunseki Kagaku, vol. 50, No. 7, 475-479 (2001).

* cited by examiner

SULFONATE COMPOUND AND FLUORESCENT PROBE USING THE SAME

TECHNICAL FIELD

The present invention relates to a sulfonate compound and a fluorescent probe using the same.

BACKGROUND ART

In recent years, it has been revealed that various diseases are caused by increased generation of active oxygen species in a living body. Thus, dynamic analyses of active oxygen species in vivo are important in clarifying causes, states, and the like of diseases. In the analyses of active oxygen species, a bio-imaging method using a fluorescent probe plays a predominant role. As fluorescent probes used for detecting hydrogen peroxide, compounds such as dichlorofluorescin (which is the reduced form of dichlorofluorescein), dihydrorhodamine 123, and Amplex Red represented by the following formulas, for example, have been developed, and such compounds have been used for various purposes. The fluorescence mechanism of these compounds is based on an oxidation reaction caused by hydrogen peroxide in the presence of a peroxidase or a peroxidase-like enzyme.

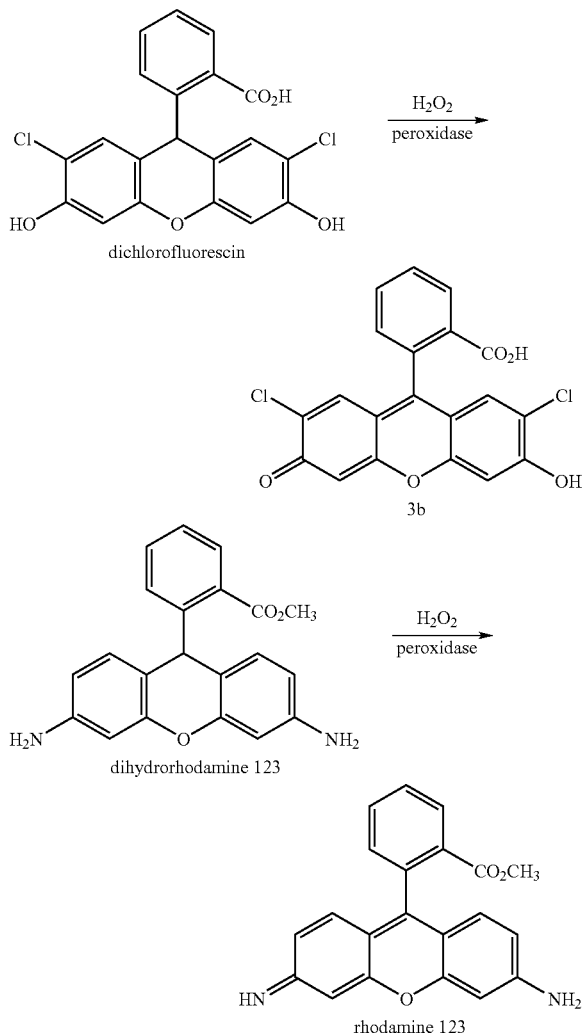

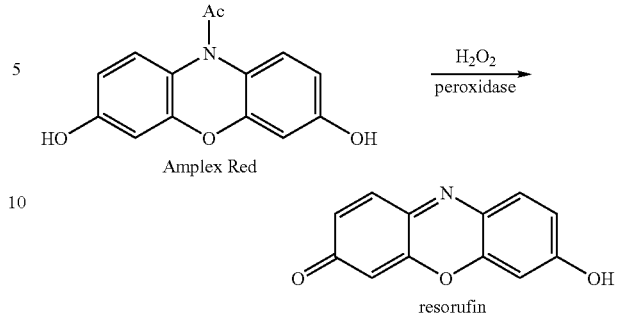

However, not only hydrogen peroxide but also many kinds of active oxygen species serve as an oxidizing agent. Accordingly, it is considered that the above-described conventional fluorescent probes evaluate the total amount of oxidizing agents, including various oxygen species, generated in a living body rather than the amount of hydrogen peroxide generated in the same. Indeed, it has been reported that these probes respond to active oxygen species other than hydrogen peroxide (e.g., singlet oxygen, hydroxyl radicals, and peroxynitrite) and to various hemoproteins having oxidizing ability. Moreover, it has been pointed out that these probes might overestimate the amount of hydrogen peroxide because these probes generate hydrogen peroxide by being oxidized through air oxidation.

Also, there has been known a compound that generates a fluorescent compound not through a redox reaction but through a deprotection reaction caused by hydrogen peroxide. More specifically, acylated resorufin (a non-fluorescent compound) is transformed into resorufin as a fluorescent compound through a deprotection reaction caused by hydrogen peroxide (see Non-Patent Documents 1 and 2). However, such resorufin has a drawback in that it is subjected to a simple hydrolysis in a cell system so that it still cannot respond to hydrogen peroxide selectively.

Because of this, the development of a fluorescent probe that can respond to hydrogen peroxide with high selectivity has been demanded from the viewpoint of cytophysiology.

Non-Patent Document 1: H. Maeda, S. Matsu-ura, M. Nishida, T. Semba, Y Yamauchi, H. Ohmori, Chem. Pharm. Bull. 2001, 49, 294-298;

Non-Patent Document 2: H. Maeda, S. Matsu-ura, M. Nishida, Y Yamauchi, H. Ohmori, Chem. Pharm. Bull. 2002, 50, 169-174.

DISCLOSURE OF INVENTION

With the foregoing in mind, it is an object of the present invention to provide a novel organic compound applicable as a fluorescent probe and the like that respond to hydrogen peroxide with high selectivity.

In order to solve the above-described problems, the present invention provides a sulfonate compound including a structure represented by a general formula (I) below.

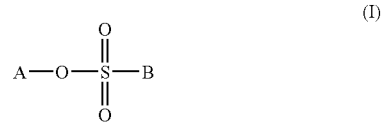

In the formula (I), an atomic group A-O is an atomic group that forms a fluorescent compound upon cleavage of a covalent bond with a sulfonyl group, there may be one or plural atomic groups B—$SO_3$— bound to an atomic group A, B is a ring substituted by one or plural electron-withdrawing groups, the electron-withdrawing group includes at least one selected from the group consisting of halogens, a carboxyl group, a carbamoyl group, a straight or branched alkylcarbamoyl group, a straight or branched alkanoyl group, a straight or branched alkoxycarbonyl group, a straight or branched alkyl halide group, and —$NR_3^+$ group (the three Rs each denote a hydrogen atom or a straight or branched alkyl group and may be the same or different), and when there are plural Bs, the Bs may be the same or different.

The sulfonate compound of the present invention has the structure represented by the general formula (I) and thus is applicable as a highly selective fluorescent probe and the like that respond only to hydrogen peroxide without responding to superoxides, hydroxyl radicals, or singlet oxygen.

DESCRIPTION OF THE INVENTION

Figure 1:
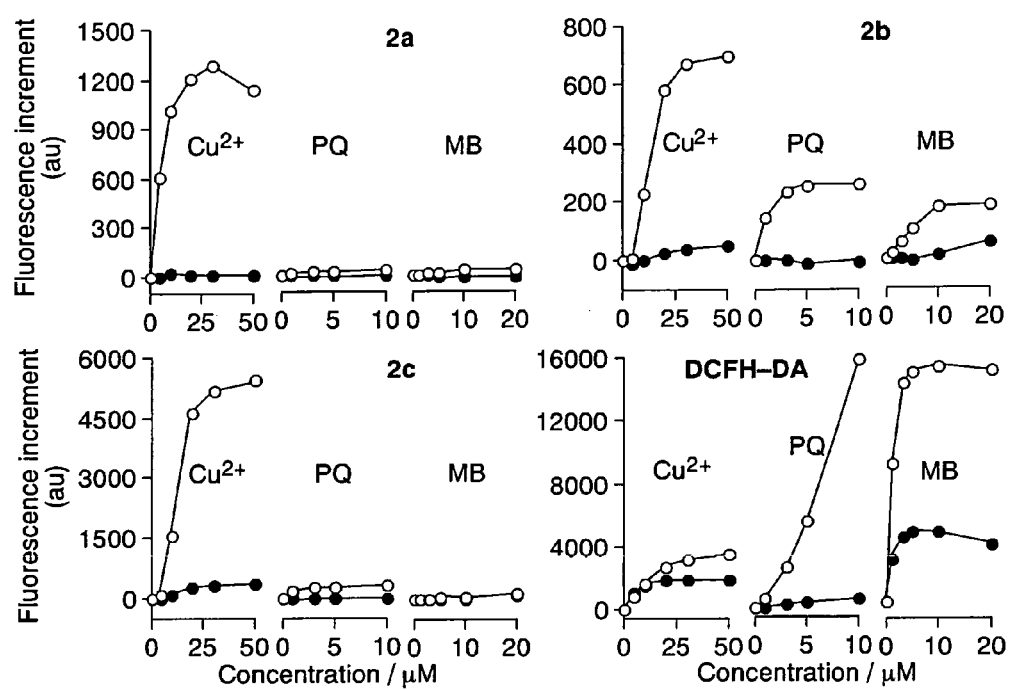
[FIG. 1] FIG. 1 contains graphs showing the results of fluorescence response exhibited by compounds 2a to 2c, respectively, in a cell system.

The above-described conventional fluorescent probes such as dichlorofluorescin (which is the reduced form of dichlorofluorescein), dihydrorhodamine 123, and Amplex Red utilize a redox reaction. In contrast, a compound of the general formula (I) according to the present invention utilizes a completely different mechanism, in which fluorescence is caused when the atomic group A-O is released upon cleavage of the covalent bond with the sulfonyl group. As described above, acylated resorufin, which is one example of a compound causing fluorescence upon deprotection by hydrogen peroxide, has a drawback in that it is subjected to a simple hydrolysis in a cell system so that it cannot selectively respond to hydrogen peroxide. The inventors of the present invention conducted in-depth research also with regard to this problem, and as a result of trial-and-error molecular designing, the inventors discovered the structure of the general formula (I), thereby arriving at the present invention. Thus, it became possible to provide a highly selective fluorescent probe that responds only to hydrogen peroxide without responding to superoxides, hydroxyl radicals, or singlet oxygen.

Hereinafter, embodiments of the present invention will be described.

An atomic group B in the above formula (I) is a ring substituted by one or plural electron-withdrawing groups, as described above. However, it is preferable that the atomic group B is an aromatic ring or a heteroaromatic ring substituted by one or plural electron-withdrawing groups from the viewpoint of the hydrogen peroxide detectability of the sulfonate compound. More specifically, when the ring forming the atomic group B is an aromatic ring or a heteroaromatic ring, the deprotection reaction caused by hydrogen peroxide proceeds more rapidly so that it is expected that still more excellent detectability can be achieved. The number of atoms in the atomic group B is not particularly limited, but the atomic group B may include a 5- to 30-membered ring, for example.

In the atomic group B in the formula (I), the electron-withdrawing group preferably includes at least one selected from the group consisting of halogens, a carboxyl group, a carbamoyl group, a straight or branched alkylcarbamoyl group with a carbon number of 1 to 6, a straight or branched alkanoyl group with a carbon number of 1 to 6, a straight or branched alkoxycarbonyl group with a carbon number of 1 to 6, a straight or branched alkyl halide group with a carbon number of 1 to 6, and —$NR_3^+$ group (the three Rs each denote a hydrogen atom or a straight or branched alkyl group with a carbon number of 1 to 6 and may be the same or different). More preferably, the electron-withdrawing group is at least one selected from the group consisting of a fluoro group, a trifluoromethyl group, and a —$N^+(CH_3)_3$ group. Among these, a fluoro group is particularly preferable. It is to be noted that the atomic group B further may be substituted by an arbitrary group excluding the electron-withdrawing group, e.g., a methyl group, an isopropyl group, or a methoxy group, if necessary. It also is to be noted that an alkyl halide group, a nitro group, and a cyano group may or may not be included in the atomic group B. The alkyl halide group preferably is a perfluoro alkyl group, more preferably a straight or branched perfluoro alkyl group with a carbon number of 1 to 6, for example. More specific examples of the alkyl halide group include perfluoro alkyl groups derived from alkyl groups such as a methyl group, an ethyl group, an n-propyl group, an isopropyl group, an n-butyl group, an isobutyl group, a sec-butyl group, and a tert-butyl group. Among these, a trifluoromethyl group is particularly preferable. Furthermore, in the atomic group B, the aromatic ring or heteroaromatic ring preferably is at least one selected from the group consisting of a benzene ring, a naphthalene ring, an anthracene ring, a pyrene ring, a pyridine ring, a pyrrole ring, a thiophene ring, a furan ring, a benzopyridine ring, a benzopyrrole ring, a benzothiophene ring, and a benzofuran ring.

In the formula (I), it is preferable that the atomic group B is at least one selected from the group consisting of a pentafluorophenyl group, a 2,4,6-trifluorophenyl group, a 2,4,6-tris(trifluoromethyl)phenyl group, and a 2,4-bis(trifluoromethyl)phenyl group from the viewpoint of the sensitivity, $H_2O_2$ selectivity, etc. of the fluorescent probe. From the similar viewpoint, it is particularly preferable that the atomic group B is at least one of a pentafluorophenyl group and a 2,4,6-trifluorophenyl group. However, it is to be noted that various kinds of groups other than those described above also are applicable as the atomic group B.

In the atomic group A-O in the above formula (I), it is preferable that an O atom is bound directly to an aromatic ring or a heteroaromatic ring, for example. The number of atoms constituting the aromatic ring or the heteroaromatic ring is not particularly limited, but the aromatic ring or the heteroaromatic ring may be a 5- to 30-membered ring, for example.

The fluorescent compound formed upon the cleavage of the covalent bond between the atomic group A-O and the sulfonyl group preferably is, for example, fluorescein, resorufin, 7-hydroxycoumarin, 1-naphthol, 2-naphthol, 1-hydroxyanthracene, 2-hydroxyanthracene, 9-hydroxyanthracene, 1-hydroxypyrene, 1-hydroxyacridine, 2-hydroxyacridine, 9-hydroxyacridine, 2-hydroxyquinolone, 4-hydroxyquinolone, 5-hydroxyquinolone, 6-hydroxyquinolone, 8-hydroxyquinolone, 4-hydroxy-7-nitro-2-oxa-1,3-diazole, or a derivative thereof. It is to be noted, however, the fluorescent compound is not limited thereto and may be a fluorescent compound of any kind. Among these, specific examples of a particularly preferable fluorescent compound include fluorescein, 2,7-dichlorofluorescein, 2,7-difluorofluorescein, 4,5-difluorofluorescein, 2,4,5,7-tetrafluorofluorescein, 2,7-dimethylfluorescein, 4,5-dimethylfluorescein, 2,4,5,7-tetramethylfluorescein, 2,7-diisopropylfluorescein, 2,7-di-t-butylfluorescein, 2,7-dimethoxyfluorescein, 2,4-difluoro-5,7-dimethylfluorescein, carboxyfluorescein, carboxy-2,7-dichlorofluorescein, carboxy-2,4,5,7-tetrachlorofluorescein, carboxy-2,7-difluorofluorescein, carboxy-2,4,5,7-tetrafluorofluoresceine, resorufin, 2,8-dichlororesorufin, 7-hydroxy-4-(trifluoromethyl)coumarin, and 7-hydroxy-4-methylcoumarin.

Particularly preferable examples of the sulfonate compound according to the present invention include those represented by formulae 1, 2, 4, and 5 below.

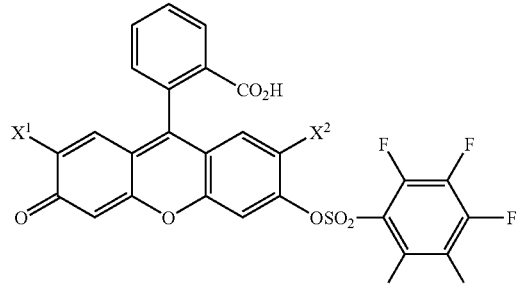

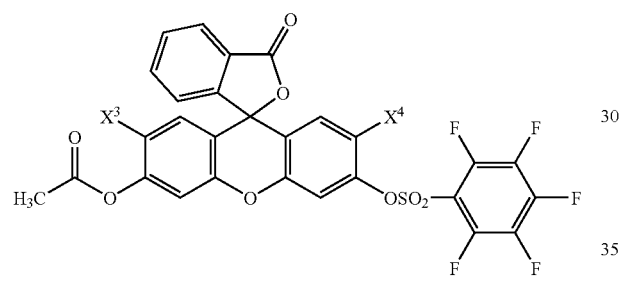

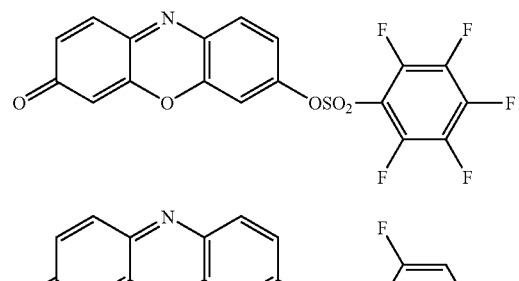

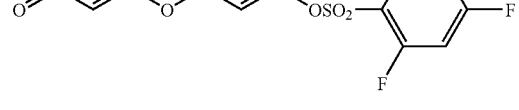

In the formulae 1 and 2, $X^1$ to $X^4$ each denote a hydrogen atom or a halogen and may be the same or different.

There is no particular limitation on the method for producing the sulfonate compound of the present invention represented by the general formula (I), and any known methods for producing a sulfonate compound can be used as appropriate. For example, the sulfonate compound of the present invention can be produced by a production method including the step of combining a compound represented by a formula (II) below and a compound represented by a formula (III) below.

$$A\text{---}OH \quad (II)$$

$$X^5\text{---}\underset{\underset{O}{\|}}{\overset{\overset{O}{\|}}{S}}\text{---}B \quad (III)$$

In the formula (III), $X^5$ is a halogen, and A and B are the same as those in the above formula (I). As the compound of the above formula (II), the fluorescent compounds listed above and the like can be used, for example, and preferable fluorescent compounds are as described above, for example. More specifically, as the compound of the formula (II), fluorochromes such as fluorescein and derivatives thereof, resorufin, 7-hydroxy-4-(trifluoromethyl)coumarin, and 7-hydroxy-4-methylcoumarin represented by formulae below can be used, for example. However, the compound of the formula (II) is not limited thereto, and various kinds of compounds can be used as the compound of the formula (II).

-continued

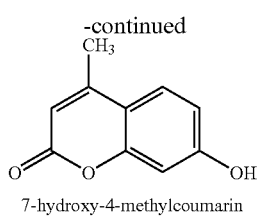

7-hydroxy-4-methylcoumarin

It is to be noted that the term "halogen" as used in the present invention represents an arbitrary halogen atom, and may be, for example, fluorine, chlorine, bromine, or iodine. An alkyl group is not particularly limited, and examples thereof includes a methyl group, an ethyl group, an n-propyl group, an isopropyl group, an n-butyl group, an isobutyl group, a sec-butyl group, and a tert-butyl group. The same applies to a group containing an alkyl group in its structure (e.g., an alkylcarbamoyl group, an alkoxycarbonyl group, or the like). An alkanoyl group is not particularly limited, and examples thereof include a formyl group, an acetyl group, a propionyl group, an isobutyryl group, a valeryl group, and an isovaleryl group. It is to be noted that an alkanoyl group with a carbon number of 1 refers to a formyl group.

In the case where the compound represented by the above formula (I) has an isomer such as a tautomer, a stereoisomer, or an optical isomer, the compound of the present invention encompasses the isomer. Moreover, in the case where any of the compound of the formula (I) and other compounds according to the present invention can form a salt, the compound of the present invention encompasses the salt. The salt is not particularly limited, and may be, for example, an acid addition salt or a base addition salt. Furthermore, an acid forming the acid addition salt may be an inorganic acid or an organic acid, and a base forming the base addition salt may be an inorganic base or an organic base. The inorganic acid is not particularly limited, but may be, for example, sulfuric acid, phosphoric acid, hydrochloric acid, hydrobromic acid, hydriodic acid, or the like. The organic acid also is not particularly limited, but may be, for example, p-toluenesulfonic acid, methanesulfonic acid, oxalic acid, p-bromobenzenesulfonic acid, carbonic acid, succinic acid, citric acid, benzoic acid, acetic acid, or the like. The inorganic base is not particularly limited, but may be, for example, ammonium hydroxide, an alkali metal hydroxide, an alkaline-earth metal hydroxide, a carbonate, a hydrogencarbonate, or the like, and more specifically is sodium hydroxide, potassium hydroxide, potassium carbonate, sodium carbonate, sodium hydrogen carbonate, potassium hydrogen carbonate, calcium hydroxide, calcium carbonate or the like. The organic base also is not particularly limited, but may be, for example, ethanolamine, triethylamine, tris(hydroxymethyl)aminomethane, or the like.

Also, there is no particular limitation on the method for producing a salt of the compound of the present invention. For example, the salt can be produced by adding the acid or the base as described above to the compound of the present invention as appropriate by a known method.

There is no particular limitation on the use of the sulfonate of the present invention, but the sulfonate of the present invention is suitable as a fluorescent probe, particularly as a fluorescent probe for detecting hydrogen peroxide (hereinafter also referred to as a "hydrogen peroxide-detecting fluorescent probe"). The fluorescent probe of the present invention includes the sulfonate compound of the present invention and thus exhibits high selectivity with respect to hydrogen peroxide.

The specificity (selectivity) of the fluorescent probe using the sulfonate compound of the present invention is not particularly limited, but preferably is as follows, for example. That is, the fluorescence response to hydrogen peroxide preferably is at least 5 times, more preferably at least 10 times, and particularly preferably at least 50 times that to a superoxide. The fluorescence response to hydrogen peroxide is, for example, not more than 100 times that to a superoxide, though the upper limit thereof is not particularly limited. Furthermore, the fluorescence response to hydrogen peroxide preferably is at least 5 times, more preferably at least 10 times, and particularly preferably at least 50 times that to a hydroxyl radical. The fluorescence response to hydrogen peroxide is, for example, not more than 100 times that to a hydroxyl radical, though the upper limit thereof is not particularly limited. Furthermore, the fluorescence response to hydrogen peroxide preferably is at least 5 times, more preferably at least 10 times, and particularly preferably at least 50 times that to glucose, ascorbic acid, 1,4-hydroquinone, propylamine, or diethylamine. The fluorescence response to hydrogen peroxide is, for example, not more than 100 times that to any of these substances, though the upper limit thereof is not particularly limited. The fluorescence response to hydrogen peroxide preferably is at least 5 times, more preferably at least 10 times, and particularly preferably at least 50 times that to a system including cytochrome P450 reductase +NADPH or a system including diaphorase +NADH. The fluorescence response to hydrogen peroxide is, for example, not more than 100 times that to any of these systems, though the upper limit thereof is not particularly limited. Note here that these values are based on the comparison of the fluorescence responses to equimolar amounts of hydrogen peroxide and each of the substances under conditions of a measurement temperature of 37° C., an excitation wavelength of 485±20 nm, and an emission wavelength of 530±25 nm. It should be noted, however, that the conditions of the measurement using the fluorescent probe of the present invention are by no means limited thereto, and the measurement can be carried out under any measurement conditions.

There is no particular limitation on the use of the fluorescent probe of the present invention, and the fluorescent probe of the present invention can be used for any purposes. For example, it can be used for bio-imaging, and it is possible to provide a bio-imaging kit by preparing a kit including the fluorescent probe of the present invention as appropriate. A method of detecting hydrogen peroxide by the use of the fluorescent probe of the present invention can achieve excellent sensitivity and excellent accuracy and thus can be applied suitably to a bio-imaging method and the like. Therefore, the sulfonate compound of the present invention also is suitable as a clinical analysis reagent and the like.

Furthermore, the present invention also provides a labeled antibody including the probe for detecting hydrogen peroxide according to the present invention as a label. As preparation of such a labeled antibody of the present invention, an antibody may be bound to the atomic group A of the sulfonate compound of the general formula (I), for example. Thus, the labeled antibody that causes fluorescence upon cleavage of the bond with an atomic group B—$SO_2$— can be obtained. Examples of such a labeled antibody include a compound 1' shown in Scheme 1 below, which is transformed into a fluorescent compound 3' upon cleavage of the bond with the sulfonate. It is to be noted, however, Scheme 1 is shown merely for an illustrative purpose and the present invention is by no means limited thereto.

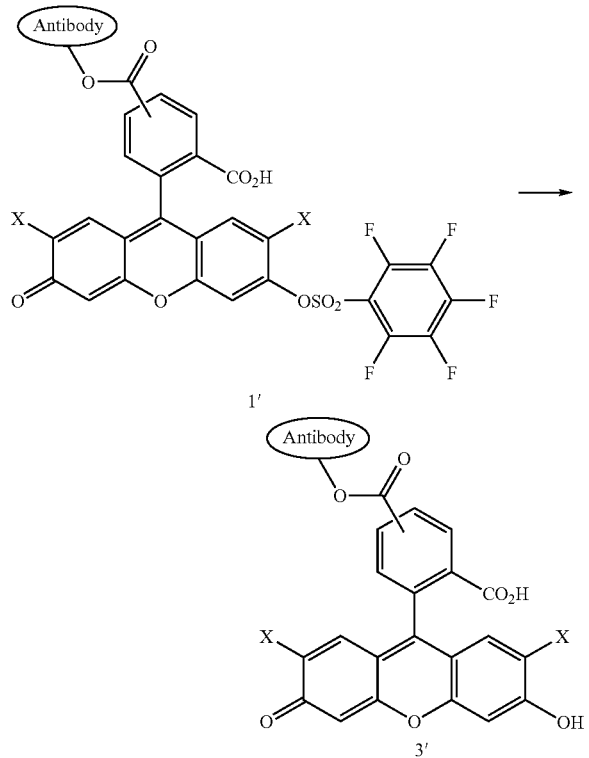

Furthermore, the hydrogen peroxide-detecting fluorescent probe according to the present invention also can be used in an assay method using blotting (transcription), an assay method using an antigen-antibody reaction, a method of quantifying catalase, a method of measuring a hydrogen peroxide scavenging ability of a functional food or a medicament, and a clinical analysis method, for example. These methods will be described more specifically below.

First, the assay method using blotting (transcription) is a method including the step of detecting a substance blotted (transcribed) on a support using the hydrogen peroxide-detecting fluorescent probe or the antibody labeled therewith according to the present invention. The substance is not particularly limited, but preferably is a protein, for example. A kit according the present invention to be used in an assay method using blotting (transcription) includes the hydrogen peroxide-detecting fluorescent probe or the antibody labeled therewith according to the present invention and a support, and optionally may include other reagents etc. as appropriate if necessary.

Specific operations, process steps, reagents to be used, etc. of the assay method using blotting are not particularly limited as long as the hydrogen peroxide-detecting fluorescent probe or the labeled antibody according to the present invention is used therein, and any known reagents, operations, etc. can be used as appropriate. As the support, agarose gel, polyacrylamide gel, a nitrocellulose film, a nylon film, or a PVDF (polyvinylidene difluoride) film, for example, can be used as appropriate, depending on the intended use of the support.

When the substance is a protein, the assay method using blotting may be, for example, a method including the steps of reacting the protein blotted on the support with a glucose oxidase-labeled antibody so as to generate a bound substance; reacting the hydrogen peroxide-detecting fluorescent probe of the present invention with hydrogen peroxide in the presence and absence of the bound substance; and quantifying the bound substance by comparing a fluorescence response obtained in the presence of the bound substance with that obtained in the absence of the bound substance.

As a method of assaying a protein using blotting, the so-called Western blot and the like have been known conventionally. However, by using the hydrogen peroxide-detecting probe according to the present invention as described above, it is possible to obtain an advantageous effect that an excellent detection sensitivity can be achieved, for example. In the above-described assay method, as a way of reacting the protein with the glucose oxidase-labeled antibody so as to generate the bound substance, it is possible to employ, for example, a method in which the protein is bound first to a primary antibody and then to the glucose oxidase-labeled antibody serving as a secondary antibody, as in the prior art.

Furthermore, when the labeled antibody of the present invention is used, the method of assaying a protein using blotting may be, for example, a method including the steps of reacting the protein blotted on the support with the labeled antibody so as to generate a bound substance; reacting the bound substance with hydrogen peroxide; and then measuring a fluorescence response obtained after the reaction between the bound substance and the hydrogen peroxide. In other words, for example, in the conventional Western blot in which a protein is bonded to a glucose oxidase-labeled antibody, the labeled antibody of the present invention may be used instead of the glucose oxidase-labeled antibody. By using the labeled antibody of the present invention as described above, it is possible to obtain an advantageous effect in that an excellent detection sensitivity can be achieved, for example.

Examples of the assay method using an antigen-antibody reaction that is carried out using the hydrogen peroxide-detecting probe of the present invention include methods described below in addition to those described above.

That is, the assay method using an antigen-antibody reaction may be, for example, an assay method including the step of causing a binding reaction between a glucose oxidase-labeled antibody and a substance to be detected, wherein the method further includes the steps of: reacting the hydrogen peroxide-detecting fluorescent probe of the present invention with hydrogen peroxide in the presence and absence of a bound substance generated through the binding reaction; and quantifying the bound substance by comparing a fluorescence response obtained in the presence of the bound substance with that obtained in the absence of the bound substance.

Heretofore, as an assay method using a glucose oxidase-labeled antibody, an assay method such as the so-called ELISA, for example, has been used widely. However, the use of the hydrogen peroxide-detecting fluorescent probe according to the present invention in such an assay method brings about an advantage that a substance to be detected can be detected with excellent detection sensitivity, for example. A kit to be used in such an assay includes the hydrogen peroxide-detecting fluorescent probe of the present invention and a glucose oxidase-labeled antibody, and optionally may include other reagents etc. as appropriate if necessary.

Alternatively, the assay method using an antigen-antibody reaction may be, for example, an assay method in which the labeled antibody of the present invention is used as a labeled antibody. Such an assay method preferably includes, for example, the steps of reacting the labeled antibody with a substance to be detected so as to generate a bound substance; reacting the bound substance with hydrogen peroxide; and measuring a fluorescence response obtained after the reaction between the bound substance and the hydrogen peroxide. In other words, the assay method may correspond to a conventional ELISA in which the labeled antibody of the present invention is used instead of a glucose oxidase-labeled antibody, for example. In the above-described assay method, as a way of reacting the substance to be detected with the labeled antibody so as to generate the bound substance, it is possible to employ, for example, a method in which the substance to be detected is bound first to a primary antibody and then to the labeled antibody serving as a secondary antibody. A kit to be used in such an assay includes the labeled antibody of the present invention, and may optionally include other reagents etc. as appropriate if necessary.

Next, a method of quantifying catalase using the hydrogen peroxide-detecting fluorescent probe of the present invention is carried out by reacting the hydrogen peroxide-detecting fluorescent probe of the present invention with hydrogen peroxide in the presence and absence of a sample containing catalase and then comparing a fluorescence response obtained in the presence of the sample with that obtained in the absence of the sample. It is possible to measure the concentration of catalase in a body fluid of a human or an animal by, for example, carrying out the above-described method of quantifying catalase using as the sample containing catalase the body fluid of the human or the animal or a sample extracted therefrom. Moreover, the method of quantifying catalase can be applied to a method of measuring a hydrogen peroxide scavenging ability of a functional food or a medicament. More specifically, the hydrogen peroxide scavenging ability of a functional food or a medicament can be measured by a method including the steps of: measuring a concentration of catalase in a body fluid of a human or an animal by the above-described method of quantifying catalase; then administering the functional food or the medicament to the human or the animal; and measuring a concentration of catalase in the body fluid of the human or the animal by the above-described method of quantifying catalase again after the administration. A kit suitable for each of these measurement methods can be obtained by designing a kit including a hydrogen peroxide-detecting probe of the present invention as appropriate.

Various clinical analyses become possible by carrying out an assay for a human or an animal by the assay method using blotting (transcription), the assay method using an antigen-antibody reaction, the method of quantifying catalase, and the method of measuring a hydrogen peroxide scavenging ability of a functional food or a medicament as described above. Thus, the sulfonate compound of the present invention is suitable as a clinical analysis reagent as described above. Moreover, by designing a kit including such a clinical analysis reagent as appropriate, it is possible to provide a clinical analysis kit suitable for various purposes.

Hereinafter, the present invention will be described more specifically by way of examples. However, it should be noted that these examples are only illustrative, and the present invention is by no means limited to these examples.that these examples are only illustrative, and the present invention is by no means limited to these examples.

EXAMPLE 1

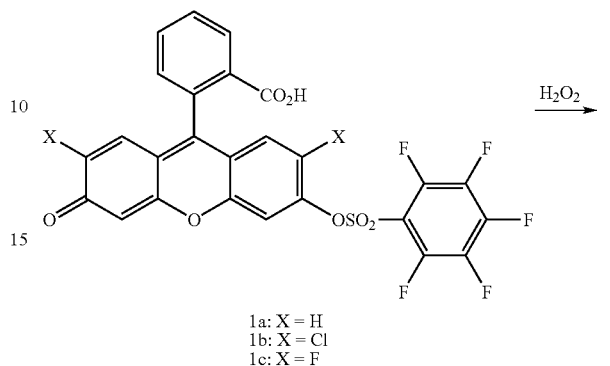

1a: X = H
1b: X = Cl
1c: X = F

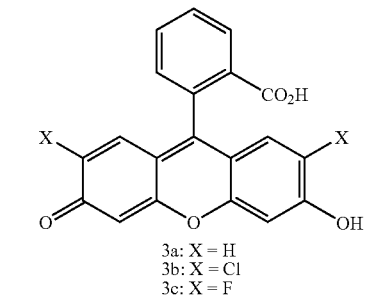

3a: X = H
3b: X = Cl
3c: X = F

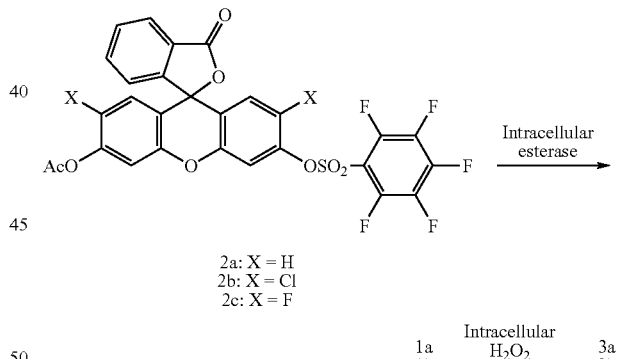

2a: X = H
2b: X = Cl
2c: X = F

1a      Intracellular    3a
1b         $H_2O_2$     3b
1c         ⟶      3c

In the present example, O-pentafluorobenzenesulfonyl forms 1a to 1c (non-fluorescent compounds) of fluoresceines 3a to 3c as fluorescent compounds shown in the above Scheme 2 were synthesized. Then, the present example demonstrated that each of the compounds 1a to 1c could serve as a highly selective fluorescent probe that responds only to hydrogen peroxide without responding to superoxides, hydroxyl radicals, or singlet oxygen, based on a totally novel fluorescence reaction resulting from a simple deprotection. Furthermore, acetylated forms 2a to 2c (Scheme 3) of the compounds 1a to 1c were synthesized. Then, the present example demonstrated that each of the compounds 2a to 2c, especially the compounds 2a and 2c, could serve as a fluorescent probe for detecting hydrogen peroxide generated intracellularly and could selectively detect intracellular oxidation stress caused by hydrogen peroxide in a freshwater green alga *Chlamydomonas reinhardtii*. Furthermore, the compounds 4 and 5 shown above also were synthesized.

(Measurement Conditions etc.)

Nuclear magnetic resonance (NMR) spectra were measured using EX-270 (trade name) (270 MHz during measurement of $^1$H) manufactured by JEOL as a measurement apparatus. Chemical shifts are shown in parts per million (ppm). Tetramethylsilane (TMS) was used as an internal standard at 0 ppm. Coupling constants (J) are given in hertz and the abbreviations s, d, t, q, m, and br refer to singlet, doublet, triplet, quartet, multiplet, and broad, respectively. Mass spectroscopy (MS) was conducted by high resolution mass spectrometry (HRMS)/fast atom bombardment (FAB) using JMS-700 (trade name) manufactured by JEOL. Infrared absorption (IR) spectra were measured by the KBr method using VALOR-III (trade name) manufactured by JASCO Corporation. Elementary analyses were conducted using CHN CORDER MT-5 (trade name) manufactured by Yanaco. Melting points were measured using MP-S3 (trade name) manufactured by Yanaco. For column chromatography separation, silica gel (manufactured by Merk & Co., Inc., Silica gel 60 (trade name)) was used. All chemicals were of reagent grades, and were purchased from Aldrich, Lancaster, Tokyo Kasei Kogyo Co., Ltd., Nacalai Tesque, Inc., and Wako Pure Chemical Industries, Ltd.

(Synthesis)

[Synthesis of the Compounds 1a to 1c]

The compounds 1a to 1c all were synthesized in the same manner. More specifically, they were synthesized in the following manner. First, to a suspension of a fluorescein derivative (1.0 g) corresponding to any one of the compounds 1a to 1c to be obtained in a mixture of 2,6-lutidine (5.0 ml) and dichloromethane (20 ml), pentafluorobenzenesulfonyl chloride (1.1 eq) was added at 0° C. The thus-obtained liquid mixture was stirred at room temperature over night. The reaction solution was diluted with dichloromethane (200 ml), washed with 1M hydrochloric acid (200 ml×2) and saturated saline (200 ml), and then dried over magnesium sulfate. The residue obtained by evaporating the solvent under a reduced pressure was purified by silica gel column chromatography (dichloromethane:acetone=20:1). Instrumental analytical values of the compounds 1a to 1c are shown below.

1a: 0.69 g (41%) as a yellow solid. m.p. 100° C.-116° C. (dec). $^1$H-NMR (270 MHz, CDCl$_3$, TMS): δ=8.04 (d, $^3J_{H,H}$=6.9 Hz, 1H; aromatic), 7.73-7.62 (m, 2H), 7.21 (d, $^4J_{H,H}$=2.1 Hz, 1H; aromatic), 7.17 (d, $^3J_{H,H}$=7.4 Hz, 1H; aromatic), 6.88 (dd, $^3J_{H,H}$=8.7 Hz, $^4J_{H,H}$=2.1 Hz, 1H; aromatic), 6.81 (d, $^3J_{H,H}$=8.7 Hz, 1H; aromatic), 6.76 (d, $^4J_{H,H}$=2.1 Hz, 1H; aromatic), 6.65 (d, $^3J_{H,H}$=8.6 Hz, 1H; aromatic), 6.59-6.55 (m, 1H), 5.76 (brs, 1H; OH). FTIR (KBr): ν=3340 (OH, br) 1765 (CO, s), 1736 (CO, s)cm$^{-1}$. FAB HRMS calcd for C$_{26}$H$_{12}$F$_5$O$_7$S (MH$^+$): 563.0224; found: 563.0223.

1b: 0.36 g (23%) as a yellow solid. m.p. 107° C.-125° C. (dec). $^1$H-NMR (270 MHz, CDCl$_3$, TMS): δ=8.07 (d, $^3J_{H,H}$=6.6 Hz, 1H; aromatic), 7.78-7.68 (m, 2H), 7.46 (s, 1H; aromatic), 7.18 (d, $^3J_{H,H}$=6.8 Hz, 1H; aromatic), 6.98 (s, 1H; aromatic), 6.83 (s, 1H; aromatic), 6.75 (s, 1H; aromatic), 5.99 (brs, 1H; OH). FTIR (KBr): ν=3324 (OH, br) 1768 (CO, s), 1736 (CO, s)cm$^{-1}$. FAB HRMS calcd for C$_{26}$H$_{10}$Cl$_2$F$_5$O$_7$S (MH$^+$): 630.9444; found: 630.9417.

1c: 0.37 g (23%) as a yellow solid. m.p. 90° C.-104° C. (dec). $^1$H-NMR (270 MHz, CDCl$_3$, TMS): δ=8.05 (d, $^3J_{H,H}$=6.8 Hz, 1H; aromatic), 7.77-7.66 (m, 2H), 7.39 (d, $^3J_{H,H}$=6.3 Hz, 1H; aromatic), 7.18 (d, $^4J_{H,F}$=7.1 Hz, 1H; aromatic), 6.95 (d, $^4J_{H,F}$=7.4 Hz, 1H; aromatic), 6.57 (d, 3J$_{H,F}$=10.1 Hz, 1H; aromatic), 6.49 (d, $^3J_{H,F}$=10.4 Hz, 1H; aromatic), 5.79 (brs, 1H; OH). FTIR (KBr): ν=3310 (OH, br), 1768 (CO, s), 1748 (CO, s)cm$^{-1}$. FAB HRMS calcd for C$_{26}$H$_{10}$F$_7$O$_7$S (MH$^+$): 599.0035; found: 599.0027.

[Synthesis of the Compounds 2a to 2c]

The compounds 2a to 2c were all synthesized in the same manner. More specifically, they were synthesized in the following manner. First, out of the compounds 1a to 1c, the compound corresponding to any one of the compounds 2a to 2c to be obtained was synthesized in the above-described manner. Then, to a solution of 0.5 g of this compound and acetyl chloride (1.1 eq) in dichloromethane, triethylamine (1.1 eq) was added at 0° C. The thus-obtained liquid mixture was stirred at room temperature for 2 hours. The reaction solution was diluted with dichloromethane (200 ml), washed with 1M hydrochloric acid (200 ml) and saturated saline (200 ml), and then dried over magnesium sulfate. The residue obtained by evaporating the solvent under a reduced pressure was purified by silica gel column chromatography (dichloromethane). Instrumental analytical values of the compounds 2a to 2c are shown below.

2a: 0.51 g (95%) as a white solid. m.p. 209° C.-210° C. $^1$H-NMR (270 MHz, [D$_6$]DMSO, TMS): δ=8.06 (d, 3J$_{H,H}$=7.3 Hz, 1H; aromatic), 7.86-7.74 (m, 2H), 7.51 (d, $^4J_{H,H}$=2.1 Hz, 1H; aromatic), 7.41 (d. $^3J_{H,H}$=7.3 Hz, 1H; aromatic), 7.27 (s, 1H; aromatic), 7.07 (dd, $^3J_{H,H}$=8.7 Hz, $^4J_{H,H}$=2.1 Hz, 1H; aromatic), 6.97-6.89 (m, 3H), 2.29 (s, 3H; CH$_3$). FTIR (KBr): ν=1771 (CO, s)cm$^{-1}$. Elemental analysis (%) calcd for C$_{28}$H$_{13}$F$_5$O$_8$S: C, 55.64; H, 2.17. found: C, 55.63; H, 2.36. FAB HRMS calcd for C$_{26}$H$_{14}$F$_5$O$_8$S (MH$^+$): 605.0330; found: 605.0331.

2b: 0.49 g (92%) as a white solid. m.p. 120° C.-124° C. (dec). $^1$H-NMR (270 MHz, [D$_6$]DMSO, TMS): δ=8.06 (d, $^3J_{H,H}$=7.3 Hz, 1H; aromatic), 7.87-7.76 (m, 2H), 7.76 (s, 1H; aromatic), 7.53 (s, 1H; aromatic), 7.49 (s, 1H; aromatic), 7.24 (s, 1H; aromatic), 7.08 (s, 1H; aromatic), 2.36 (s, 3H; CH$_3$). FTIR (KBr): ν=1775 (CO, s)cm$^{-1}$. Elemental analysis (%) calcd for C$_{28}$H$_{11}$Cl$_2$F$_5$O$_8$S: C, 49.94; H, 1.65. found: C, 49.96; H, 1.84. FAB HRMS calcd for C$_{28}$H$_{12}$Cl$_2$F$_5$O$_8$S (MH$^+$): 672.9550; found: 672.9549.

2c: 0.47 g (87%) as a white solid. m.p. 213° C.-214° C. $^1$H-NMR (270 MHz, [D$_6$]DMSO, TMS): δ=8.05 (d, 3J$_{H,H}$=7.1 Hz, 1H; aromatic), 7.85-7.74 (m, 2H), 7.76 (d, $^4J_{H,F}$=6.4 Hz, 1H; aromatic), 7.47 (d. $^4J_{H,F}$=6.4 Hz, 1H; aromatic), 7.43 (d, $^3J_{H,H}$=7.4 Hz, 1H; aromatic), 7.13 (d, $^3J_{H,F}$=10.2 Hz, 1H; aromatic), 6.95 (d, $^3J_{H,F}$=10.2 Hz, 1H; aromatic), 2.35 (s, 3H; CH$_3$). FTIR (KBr): ν=1778 (CO, s)cm$^{-1}$. Elemental analysis (%) calcd for C$_{28}$H$_{11}$F$_7$O$_8$S: C, 52.51; H, 1.73. found: C, 52.60; H, 1.99. FAB HRMS calcd for C$_{28}$H$_{12}$F$_7$O$_8$S (MH$^+$): 641.0141; found: 641.

[Synthesis of the Compounds 4 and 5]

The compounds 4 and 5 were synthesized in the same manner. More specifically, they were synthesized in the following manner. First, to a suspension of resorufin sodium salt (2.0 g) in pyridine (20 ml), pentafluorobenzenesulfonyl chloride or 2,4,6-trifluorobenzenesulfonyl chloride (1.1 eq) was added at −40° C. The thus-obtained liquid mixture was stirred at a temperature from −40° C. to −20° C. for 6 hours. The reaction solution was diluted with dichloromethane (200 ml), washed with 1M hydrochloric acid (200 ml×2) and saturated saline (200 ml), and then dried over magnesium sulfate. The residue obtained by evaporating the solvent under a reduced pressure was purified by silica gel column chromatography (dichloromethane:acetone=20:1). Instrumental analytical values of the compounds 4 and 5 are shown below.

4: 1.7 g (45%) as an orange crystal. m.p. 200° C.-201° C. (from AcOEt). $^1$H-NMR (270 MHz, CDCl$_3$, TMS): δ=7.82 (d, $^3J_{H,H}$=8.6 Hz, 1H; aromatic), 7.43 (d, $^3J_{H,H}$=9.9 Hz, 1H; aromatic), 7.24-7.19 (m, 2H; aromatic), 6.88 (dd, $^3J_{H,H}$=9.9 Hz, $^3J_{H,H}$=2.0 Hz, 1H; aromatic), 6.34 (d, $^4J_{H,H}$=2.0, 1H; aromatic), 6.49 (dd, $^3J_{H,F}$=10.1 Hz, $^4J_{H,F}$=2.4 Hz, 2H; aromatic). FTIR (KBr): ν=1624 (CO, s)cm$^{-1}$. Elemental analysis (%) calcd for C$_{18}$H$_6$F$_5$NO$_5$S: C, 48.77; H, 1.36; N, 3.16; S, 7.23; F, 21.43. found: C, 48.69; H, 1.54; N, 3.02, S, 7.00; F, 21.38.

5: 2.2 g (64%) as an orange crystal. m.p. 204° C.-207° C. (from AcOEt). $^1$H-NMR (270 MHz, CDCl$_3$, TMS): δ=7.79 (d, $^3J_{H,H}$=8.2 Hz, 1H; aromatic), 7.42 (d, $^3J_{H,H}$=9.9 Hz, 1H; aromatic), 7.22-7.18 (m, 2H; aromatic), 6.91-6.84 (m, 3H; aromatic), 6.32 (d, $^4J_{H,H}$=2.0 Hz, 1H; aromatic). FTIR (KBr): ν=1624 (CO, s)cm$^{-1}$. Elemental analysis (%) calcd for C$_{18}$H$_8$F$_3$NO$_5$S: C, 53.08; H, 1.98; N, 3.44. found: C, 53.07; H, 2.14; N, 3.17. FAB HRMS calcd for C$_{18}$H$_9$F$_3$NO$_5$S (MH$^+$): 408.0154; found: 408.0158.

(Evaluation of H$_2$O$_2$ Selectivity of the Compound 1)

Each of the compounds 1a, 1b, and 1c shown in Scheme 2 exhibited H$_2$O$_2$ concentration-dependent response in a 96-well microplate assay. In this assay, a DMSO solution of the compound 1a (10 mM), a DMSO solution of the compound 1b (2 mM), and a DMSO solution of the compound 1c (2 mM) were provided first and then these solutions were diluted 400-fold with a HEPES buffer solution (pH 7.4, 10 mM). Thus, probe solutions of the respective compounds were prepared. In the respective probe solutions, the concentration of the compound 1a was 25 µM, the concentration of the compound 1b was 5 µM, and the concentration of the compound 1c was 5 µM. Then, 150 µl of each of the probe solutions was allowed to react with H$_2$O$_2$ water (0.92 mM, 10 µl) at 25° C. for 60 minutes. The detection limits of the compounds 1a, 1b, and 1c were 46.0 (RSD, n=8; 1.2%), 23.1 (0.5%), and 4.6 (1.0%) pmol, respectively, which are all acceptable for cellular level detection. With regard to each of the compounds 1a, 1b, and 1c, a linear calibration curve with a correlation coefficient of at least 0.999 was obtained when the detected value was in the range from the detection limit to 92.3 nmol. The linear calibration curves with regard to the compounds 1a, 1b, and 1c respectively exhibited the slopes of 172, 215, and 591 au/nmol.

The fluorescence response to H$_2$O$_2$ achieved by each of the thus-obtained compounds 1a, 1b, and 1c was compared with that to HO. (a hydroxyl radical) and that to O$_2^-$. (a superoxide). As a source of HO., the Fenton reaction between H$_2$O$_2$ (1 mM, 10 µl) and Fe$^{2+}$ (5 mM, 10 µl) was used. On the other hand, O$_2^-$. was generated by causing an enzyme reaction between hypoxanthine (HPX) (1 mM, 10 µl) and xanthine oxidase (XO) (0.26 U/ml, 10 µl). The results are shown in Table 1.

In Table 1, fluorescence responses observed after reacting the compounds 1a, 1b, and 1c with H$_2$O$_2$, HO., or O$_2^-$. were compared with each other. Numbers in Table 1 represent the fluorescence intensity (RFU). Note here that the RFU is a value obtained by subtracting a fluorescence intensity obtained in the absence of H$_2$O$_2$ or HPX from the measured value.

TABLE 1

| | Fluorescence Intensity (RFU) | | |
|---|---|---|---|
| | 1a | 1b | 1c |
| H$_2$O$_2$ | 1150 | 2193 | 4375 |
| H$_2$O$_2$ + Fe$^{2+}$ | 28 | 195 | 184 |
| HPX + XO | 566 | 1733 | 3580 |
| HPX + XO + catalase | −49 | −51 | −44 |
| HPX + XO + SOD | 899 | 1733 | 3340 |

The responses to HO. achieved by the compounds 1a, 1b, and 1c were much smaller than those to H$_2$O$_2$. Although the fluorescence responses achieved by the compounds 1a, 1b, and 1c in the HPX-XO system were eliminated completely by the addition of catalase (5000 U/ml, 10 µl), they were maintained or increased in the presence of superoxide dismutase (SOD) (1000U/mil, 10 µl). These results show that each of the compounds 1a, 1b, and 1c can serve as a fluorescent probe that responds to H$_2$O$_2$ with higher selectivity than to HO. and O$_2^-$..

(Evaluation of H$_2$O$_2$ Selectivity of the Compounds 2 in Alga Cells)

Photic stimulation can cause oxidative stress in green algae. Stimulation with Cu$^{2+}$ causes intracellular generation of various ROS such as superoxides, hydrogen peroxide, and hydroxyl radicals. Furthermore, when alga cells are activated specifically by paraquat (PQ) or methylene blue (MB), oxidative stress can be caused by the generation of a superoxide or $^1$O$_2$. Thus, an experimental model using a freshwater green alga *Chlamydomonas reinhardtii* was useful in evaluating the applicability of the probe of the present invention to cell systems. In order to load alga cells with the compounds 1a, 1b, and 1c, the derivatives 2a, 2b, and 2c (Scheme 3) as acetylated forms of the compounds 1a, 1b, and 1c were used. By conducting a microplate assay similar to that described above, it was confirmed that esterase was necessary to allow the compounds 2a, 2b, and 2c to serve as a hydrogen peroxide-detecting probe.

More specifically, first, the compounds 2a, 2b, and 2c respectively were dissolved in DMSO, thus obtaining 10 mM stock solutions of the respective compounds. Next, *Chlamydomonas reinhardtii* (IAM C-238) cultured by an ordinary method was inoculated into 3 ml of an MBM culture solution. Thereafter, the MBM culture solution was loaded with 7.5 µl of each of the stock solutions of the compounds 2a, 2b, and 2c in the dark at 25° C. for 30 minutes. Thus, probe-loaded cell suspensions were prepared. Furthermore, a 96-well tissue culture plate was provided, and 50 µl of a MBM solution containing the indicated concentration of CuCl$_2$, PQ, or Mv was added to the plate. The probe-loaded cell suspension (50 µl) was inoculated to the plate and then incubated under irradiation with light or in the dark. After 60 minutes, fluorescence in the cells was measured using a fluorescence measuring device (trade name "CytoFluor II multiwell fluorescence plate reader", PerSeptive Biosystems, USA). For the measurement, an excitation filter was set at 485±20 nm and an emission filter was set at 530±25 nm.

FIG. 1 contains graphs showing the results of fluorescence response exhibited by the compounds 2a to 2c, respectively, in a cell system. FIG. 1 contains graphs showing the correlation between a concentration and a fluorescence increment when the fluorescence response was measured by loading *Chlamydomonas reinhardtii* cells with the compound 2a, 2b, or 2c (25 µM) or DCFH-DA (50 µM) in the dark at 25° C. for 30 minutes and incubating them in 96-well microplates under irradiation with light or in the dark in the presence of Cu$^{2+}$, PQ, or MB for 60 minutes. In FIG. 1, an empty circle indicates the result obtained when the incubation was carried out under irradiation with light and a solid circle indicates the result obtained when the incubation was carried out in the dark.

From the results shown in FIG. 1, it is understood that the cells loaded with the compounds 2a, 2b, and 2c exhibited fluorescence response in a stimulation concentration-dependent manner when the incubation was carried out under irradiation with light in the presence of $Cu^{2+}$. In particular, it was found that the compounds 2a and 2c had high selectivity with respect to the above-described conditions and achieved great fluorescence increments. These results indicate that the compounds 2a and 2c detected the oxidative stress derived from the intracellular generation of $H_2O_2$, rather than $O_2^-$. and $^1O_2$, resulting from the $Cu^{2+}$ stimulation and the irradiation with light. Considering the fact that the compounds 1a and 1c had a high $H_2O_2$ selectivity, it is speculated that the compounds 2a and 2c infiltrated into the cells and were transformed into the compounds 1a and 1c, respectively. In contrast to the behaviors of the compounds 2a, 2b, and 2c, DCFH-DA detected the oxidative stress caused by PQ and MB effectively and also detected ROS generated by the $Cu^{2+}$ stimulation. These results indicate that DCFH is not useful as a probe for providing an indicator of the total amount of oxidants. Thus, it was verified that the compounds 2, especially the compounds 2a and 2c, could serve as a probe in a cell system without losing their selectivities.

These results demonstrate that the compounds 1a, 1b, and 1c can serve as novel fluorescent probes exhibiting much higher selectivity with respect to $H_2O_2$ than to $O_2^-$., HO., and $^1O_2$, based on a non-oxidative mechanism. It is expected that these novel probes and their homologues facilitate the measurement of cell-derived $H_2O_2$ and thus contribute to the elucidation of dynamic functions of not only alga cells but also phagocytes and vascular endothelium cells.

As apparent from the data given in the above, in the detection of hydrogen peroxide, the compounds 1a to 1c exhibited the selectivity that had not been achieved by conventional fluorescent probes based on an oxidative fluorescence mechanism. Therefore, it is expected that the compounds 1a to 1c and their analogues can be used as a fluorescent probe with the selectivity required for cellular level analyses. As fluorescent compounds having a phenolic hydroxyl group, those with various structures and fluorescence characteristics are readily available. It is expected that O-pentafluorobenzene-sulfonyl forms of such compounds similarly can be used as a hydrogen peroxide fluorescent probe. More specifically, this can be achieved, for example, in the manner shown in Scheme 4 below. Therefore, it is believed that, by applying the fluorescence mechanism developed by the inventors of the present invention, it is possible to design and develop a fluorescent probe (and a clinical analysis reagent) having characteristics suitable for the intended use thereof.

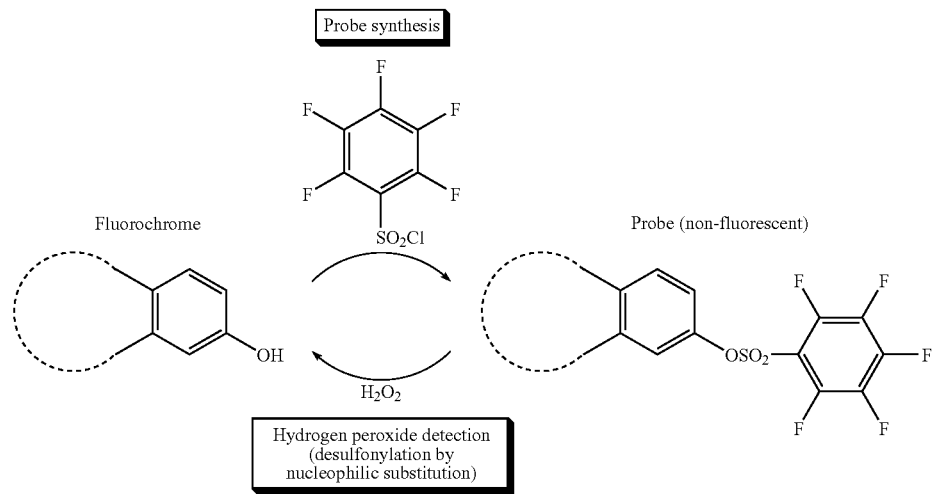

Scheme 4

INDUSTRIAL APPLICABILITY

As specifically described above, the sulfonate compound according to the present invention is suitable as a fluorescent probe that responds to hydrogen peroxide with high selectivity. The fluorescent probe is a reagent that plays an important role in the current cytophysiological research. Besides, considering the recent remarkable progress in both hardware and software for image analysis systems and flow cytometry (cell sorters) using a fluorescence microscope, it is conceivable that the fluorescent probe market will expand increasingly. The present invention is suitable for bio-imaging, clinical analyses, etc., for example, and can be used favorably to develop novel treatment methods for diseases associated with active oxygen species and seeds for novel medicaments for such diseases. The use of the sulfonate compound of the present invention is not limited to a fluorescent probe, and it can be used for any purposes.

The invention claimed is:

1. A sulfonate compound represented by a formula (I) below,

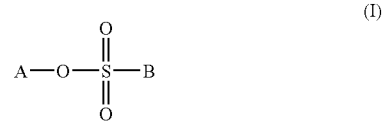

(I)

where an atomic group A-O is an atomic group that forms a fluorescent compound (excluding hydroxycoumarin and derivatives thereof) upon cleavage of a covalent bond with a sulfonyl group, there may be one or plural atomic groups B—SO$_3$— bound to an atomic group A, A is represented by a formula (X-1) or (X-2) below,

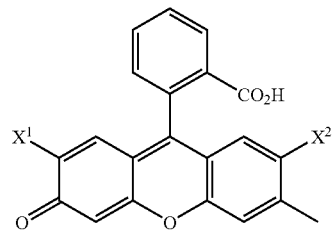

(X-1)

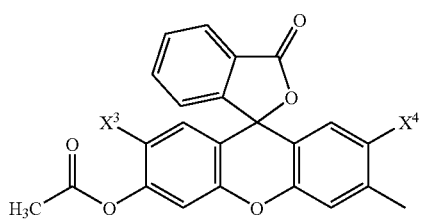

(X-2)

where, in the above formulae, $X^1$, $X^2$, $X^3$ and $X^4$ each denote a hydrogen atom or halogen atom, and may be the same or different, and an atomic group B is at least one selected from the group consisting of a pentafluorophenyl group, a 2,4,6-trifluorophenyl group, a 2,4,6-tris(trifluoromethyl)phenyl group, and a 2,4-bis(trifluoromethyl)phenyl group.

2. The sulfonate compound according to claim 1, which is represented by any one of formulae 1 and 2 below,

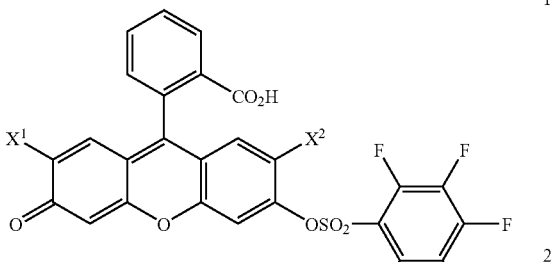

1

2 where $X^1$ to $X^4$ in the formulae 1 and 2 each denote a hydrogen atom or a halogen and may be the same or different.

3. A method for producing the sulfonate compound according to claim 1, comprising the step of combining a compound represented by a formula (II) below and a compound represented by a formula (III) below,

(II)

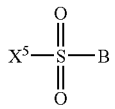

(III)

where $X^5$ in the formula (III) is a halogen, and A and B are the same as A and B in the formula (I).

* * * * *